United States Patent [19]
Granger et al.

[11] Patent Number: 5,149,538
[45] Date of Patent: Sep. 22, 1992

[54] MISUSE-RESISTIVE TRANSDERMAL OPIOID DOSAGE FORM

[75] Inventors: Colin D. Granger, Chester; Thomas H. Simon, Morris Plains, both of N.J.

[73] Assignee: Warner-Lambert Company, Morris Plains, N.Y.

[21] Appl. No.: 716,037

[22] Filed: Jun. 14, 1991

[51] Int. Cl.$^5$ .................. A61K 9/70; A61K 31/485
[52] U.S. Cl. .................. 424/449; 424/484; 424/486
[58] Field of Search .......... 424/449, 488, 487, 485, 424/484; 514/282

[56] References Cited

U.S. PATENT DOCUMENTS

| | | | |
|---|---|---|---|
| 3,996,934 | 12/1976 | Zaffaroni | 128/268 |
| 4,464,378 | 8/1984 | Hussain | 424/260 |
| 4,573,995 | 3/1986 | Chen et al. | 604/896 |
| 4,588,580 | 5/1986 | Gale et al. | 424/21 |
| 4,626,539 | 12/1986 | Aungst et al. | 514/282 |
| 4,806,341 | 2/1989 | Chien et al. | 424/448 |
| 4,917,676 | 4/1990 | Heiber et al. | 424/449 |
| 4,935,428 | 6/1990 | Lewis | 514/282 |

FOREIGN PATENT DOCUMENTS 0368409 5/1990 European Pat. Off. .
9004965 5/1990 PCT Int'l Appl. .

Primary Examiner—Thruman K. Page
Assistant Examiner—Neil S. Levy
Attorney, Agent, or Firm—Richard S. Bullitt

[57] ABSTRACT

A misuse-resistive dosage form for the transdermal delivery of opioid comprises, in combination, 1) one or more opioid permeable to the skin, 2) delivery means permeable to said opioid, 3) one or more antagonist for said opioid releasable upon ingestion or solvent immersion, and 4) impermeable barrier means separating said opioid and said antagonist.

9 Claims, 2 Drawing Sheets

MISUSE-RESISTIVE TRANSDERMAL OPIOID DOSAGE FORM

BACKGROUND OF THE INVENTION AND INFORMATION DISCLOSURE

Dosage forms for the transdermal delivery of narcotic analgesics are well known in the art. For example, U.S. Pat. No. 4,806,341, issued to Chien et al describes transdermal absorption dosage units for narcotic analgesics and antagonist comprising a backing layer, an adjoining layer of a solid polymer matrix containing morphinan narcotic analgesics or antagonist pharmaceuticals and skin permeation enhancers, and an adhesive polymer.

U.S. Pat. No. 4,626,539, issued to Aungst et al describes pharmaceutical compositions containing an opioid, a penetration enhancer such as $C_8$-$C_{18}$ fatty alcohols or fatty acids, and a pharmaceutical carrier, such as propylene glycol. The compositions may be in gel, lotion or cream form and used in a transdermal patch.

European Patent Publication No. 0368409 describes compositions for the transdermal delivery of buprenorphine salts in a carrier comprising a polar solvent of $C_3$-$C_4$ diols and/or $C_3$-$C_6$ triols and a polar lipid material such fatty alcohols and esters thereof. The compositions may be used in transdermal patches and are described as being useful for analgesic purposes.

U.S. Pat. No. 4,935,428 issued to J. Lewis describes pharmaceutical compositions in sublingual unit dosage for maintenance treatment of opiate addicts comprising from 2-8 milligrams buprenorphine and an amount of naltrexon to attenuate the effect of the buprenorphine when injected. The dosage forms of the '428 patent comprise buprenorphine and naltrexone blended together to form a homogenous mixture or solution.

U.S. Pat. No. 4,464,378 issued to A. Hussain describes dosage forms for nasal administration of narcotic antagonists and analgesics. The dosage forms can be solutions, suspensions, gels or ointments.

U.S. Pat. No. 4,573,995 issued to Chen et al describes transdermal delivery systems for the administration of naloxone, naltrexone and nalbuphine. U.S. Pat. No. 4,588,580 issued to Gale et al describes transdermal delivery systems for delivery of fentanyl and its analgetically effective derivatives.

PCT Patent Publication No. WO 90/04965 describes transdermal dosage forms for delivering narcotic and psychoactive substances which have a reduced potential for abuse. The dosage forms may be in the form of a transdermal patch having a reservoir comprising a homogenous mixture of the narcotic and antagonist, and a releasing means through which the narcotic is released to the body.

The dosage forms of the prior art have deficiencies in that an addict can extract the narcotic from the dosage form for injection or ingestion, or that the narcotic and antagonist are physically combined such that adverse physical and chemical interaction may occur. The present invention overcomes the deficiencies of the prior art dosage forms by providing a transdermal dosage form containing an opioid and an opioid antagonist, wherein the opioid and the antagonist are physically separated by an impermeable barrier. This barrier prevents undesirable ion exchange and other interactions between the opioid and the antagonist. The dosage form of this invention further provides the benefit of being resistive to misuse because the opioid antagonist is released from the dosage form upon being ingested or substantially immersed in water or other solvents. When applied to the skin, the dosage form of this invention delivers only the opioid through the skin and into the systemic circulatory system.

Thus, the dosage form of the present invention provides the following advantages:

1. A therapeutic effect which is constant;
2. Smoothness and consistency in the level of opioid delivered to the bloodstream;
3. Reduced potential for misuse or abuse of the opioid-containing dosage form;
4. Decreased risk of overdosing and resulting toxic reactions;
5. Improvements in the ability of opioid addicts to correctly and safely use opioid maintenance treatment on an outpatient, unsupervised basis;
6. Improved patient compliance with a recommended treatment program; and
7. Elimination of undesirable interactions and reactions between the opioid and the opioid antagonist contained in the dosage form.

SUMMARY OF THE INVENTION

This invention relates to an improved dosage form for the transdermal delivery of opioid which is resistive to misuse and abuse. The dosage form of the invention is capable of delivering opioid through the skin to the systemic circulatory system of a mammal for the treatment of narcotic addiction or for analgesic or other effects. The dosage form comprises, in combination:

a) delivery means through which said opioid is delivered to said systemic circulatory system by applying to the skin;

b) one or more of said opioid, said opioid being permeable through said delivery means and to the skin to which it is applied;

c) an effective amount of one or more antagonist substance sufficient to substantially attenuate the euphorigenic effect of said opioid, wherein said antagonist substance is releasable from said dosage form upon being ingested or substantially immersed in a solvent, and d) barrier means which separate said antagonist substance from said opioid, said barrier means being impermeable to said opioid and said antagonist substance.

The dosage form of this invention delivers and maintains a therapeutic level of the opioid in the bloodstream while in use, preferably at a level from about 0.1 to about 100 nanograms of opioid per milliliter of blood plasma. The impermeable barrier separates the opioid in the dosage form from the antagonist substance to prevent any adverse chemical reactions or ion exchanges between the opioid and the antagonist, and to prevent release of the antagonist unless the dosage form is ingested or immersed in water, alcohol or other solvent. If ingested or solvent extracted, the antagonist substance substantially attenuates the euphorigenic effect of the opioid, thereby reducing the tendency for misuse and abuse of the dosage form.

The preferred dosage form is a transdermal adhesive patch comprising buprenorphine or salts thereof as the opioid and naltrexone or salts thereof as the antagonist substance.

DETAILED DESCRIPTION

Figure 1:
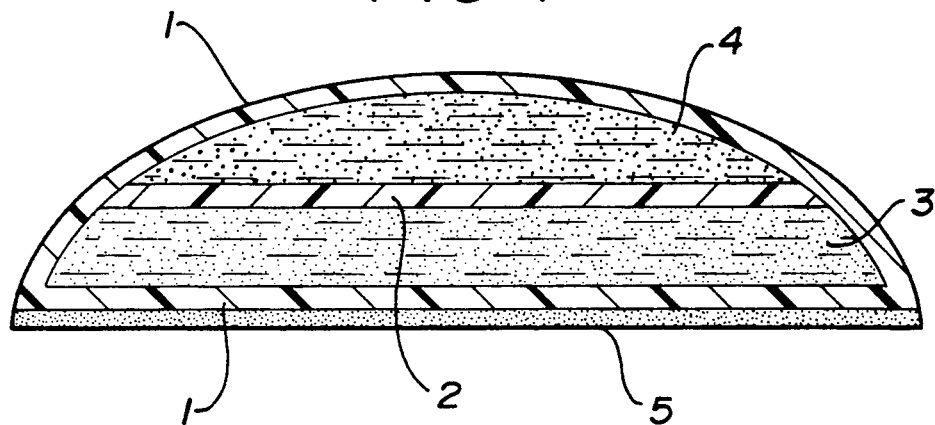
FIG. 1 shows a cross-sectional view of a dosage form of this invention comprising an adhesive layer 5 for attachment to the skin, a reservoir of opioid 3, delivery means 1 for delivering said opioid to the skin, a reservoir of opioid antagonist 4, and barrier means 2 separating said opioid and said opioid antagonist.

The present invention relates to a dosage form for the transdermal delivery of one or more opioid to the systemic circulatory system of a mammal comprising, in combination:
  a) delivery means through which said opioid is delivered to said systemic circulatory system by applying to the skin;
  b) one or more of said opioid, said opioid being permeable through said delivery means and to the skin to which it is applied;
  c) an effective amount of one or more antagonist substance sufficient to substantially attenuate the euphorigenic effect of said opioid, wherein said antagonist substance is releasable from said dosage form upon being ingested or substantially immersed in a solvent; and
  d) barrier means which separate said antagonist substance from said opioid, said barrier means being impermeable to said opioid and to said antagonist substance.

The dosage form preferably is in the nature of a transdermal patch which is applied and affixed to the skin. The dosage form is resistive to misuse and abuse, and it is useful in delivering opioid through the skin to the systemic circulatory system for opiate maintenance treatment, analgesic effect or other medicinal purposes.

The dosage form comprises a delivery means through which one or more opioid is delivered to the skin. The delivery means can comprise any layer or matrix of material which is permeable to the opioid and which allows the opioid to diffuse to the skin. Examples of suitable materials for said delivery means include polyethylene, polypropylene, ethylene/propylene copolymers, ethylene/ethylacrylate copolymers, ethylene/vinyl acetate copolymers, polyacrylates, polymethacrylates, silicone elastomers, medical-grade polydimethylsiloxanes, neoprene rubber, polyisobutylene, chlorinated polyethylene, polyvinyl chloride, vinyl chloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylene-vinyloxyethanol copolymer; silicone copolymers, for example polysiloxane-polycarbonate copolymers, polysiloxane-polyethyleneoxidecopolymers, polysiloxane-polymethacrylate copolymers, polysiloxane-alkylene copolymers (e.g., polysiloxane-ethylene copolymers), polysiloxane-alkylenesilane copolymers (e.g., polysiloxaneethylenesilane copolymers), and the like; cellulose polymers, for example methyl or ethyl cellulose, hydroxypropyl methyl cellulose, and cellulose esters; polycarbonates; polytetrafluoroethylene; starches; gelatin; natural and synthetic gums; and any other natural or synthetic polymer or fiber and combinations thereof. The delivery means can be a polymeric film which is permeable to the opioid and which forms a cavity containing a reservoir of the opioid therein.

The delivery means can comprise an adhesive matrix or layer containing the opioid dispersed therein. Preferably the adhesive layer is comprised of an adhesive prepared from polymers and copolymers of acrylic esters or methacrylic esters and copolymers of acrylic esters or methacrylic esters and other ethylenically-unsaturated monomers. Preferably the acrylic adhesive is selected from the group consisting of butyl acrylate, ethyl acrylate, ethyl hexyl acrylate, vinylacetate/ethylene acrylate and mixtures thereof. The acrylic adhesives of this invention can be prepared by conventional processes which are well known in the art, including suspension, dispersion, emulsion or solution polymerization techniques. In addition to functioning as a delivery means through which the opioid is delivered to the systemic circulatory system of a mammal, the adhesive layer firmly affixes the dosage form to the skin.

The dosage form of this invention comprises one or more opioid(s) which are permeable through the delivery means and also permeable to the skin to which the opioid is applied. By the term "opioid" is meant any natural or synthetic opioid analgesic or other narcotic analgesic or mixtures thereof. Some examples of suitable opioids useful according to this invention are alfentanil, allylprodine, alphaprodine, anileridine, benzylmorphine, bezitramide, buprenorphine, butorphanol, clonitazene, codeine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, hydrocodone, hydromorphone, hydroxypethidine, isomethadone, ketobemidone, levorphanol, lofentanil, meperidine, meptazionl, metazocine, methadone, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, phenoperidine, piminodine, piritramide, proheptazine, promedol, properidine, propiram, propoxyphene, sufentanil, tilidine, and pharmaceutically acceptable salts thereof and mixtures thereof. The most preferred opioids are morphine, buprenorphine and pharmaceutically acceptable salts thereof.

The pharmaceutically acceptable salts of the opioid useful in this invention include any of the non-toxic salts of the opioid which have pharmacologic properties, such as, for example, the hydrochloride, hydrobromide, hydroiodide, sulfate, bisulfate, nitrate, citrate, tartrate, bitartrate, lactate, phosphate, malate, maleate, fumarate, succinate, acetate, palmeate stearate, oleate, palmitate, laurate, valerate and the like.

The opioid may be contained in a gel, cream, paste, slurry or other suitable pharmaceutical carrier. Preferably one or more skin permeation enhancers are included along with the opioid. Examples of suitable permeation enhancers are described in U.S. Pat Nos. 3,989,816; 4,316,893; 4,405,616; 4,060,084; and 4,379,454; the disclosures of which are herein incorporated by reference. Preferred permeation enhancers are saturated fatty alcohols, fatty alcohol esters, or fatty acids having 8-18 carbon atoms and unsaturated fatty alcohols, fatty alcohol esters, or fatty acids having 8-18 carbon atoms. Some examples of fatty acids, fatty alcohols and fatty alcohol esters include lauric acid, oleic acid, linoleic acid, octanol, decanol, lauryl alcohol, myristyl alcohol, myristoleyl alcohol, palmitoleyl alcohol, oleyl alcohol, linolenyl alcohol, linolyl alcohol, elaidyl alcohol, vaccenyl alcohol, petroselinyl alcohol, petroselaidyl alcohol, methyl caproate, propyl caproate, hexyl acetate, methyl heptylate, pentyl heptylate, heptyl acetate, heptyl caproate, methyl caprylate, propyl caprylate, octyl acetate, octyl butylate, methyl caprate, ethyl caprate, hexyl caprate, methyl pelargonate, butyl pelargonate, lauryl acetate, lauryl butylate, methyl laurate, ethyl laurate, isopropyl laurate, hexyl laurate, $C_{12}$-$C_{18}$ alcohols lactate, methyl myristate, ethyl myristate, isopropyl myristate, pentadecyl acetate, methyl palmitate, ethyl palmitate, isopropyl palmitate, hexadecyl acetate, methyl oleate, ethyl oleate, butyl oleate, dimethyl adipate, disopropyl adipate, disobutyl adioate, dimethyl maleate, diisopropyl malate, dibutyl malate, dihexyl maleate, and mixtures thereof.

The dosage form of this invention contains one or more opioid antagonist substance. The antagonist substance is present in an effective amount to substantially attenuate the euphorigenic effect of the opioid, and it is releasable from the dosage form upon being ingested or substantially immersed in water, alcohol or other solvent. Examples of suitable antagonist substances include naltrexone, naloxone, nalorphine, nalorphine dinicotinate, nalmefene, nadide, levallorphan, cyclazocine, amiphenazole, and pharmaceutically acceptable salts and mixtures thereof. The preferred antagonist substance is naltrexone or its pharmaceutically acceptable salts.

A barrier means separate the antagonist substance from the opioid. The barrier mean must be impermeable to the antagonist substance and to the opioid to prevent these components from coming into physical or chemical contact while in the dosage form. The barrier means can be comprised of any material which is impermeable to the opioid and the antagonist substance, such as, for example, polyethylene, polypropylene, ethylene/propylene copolymers, ethylene/ethylacrylate copolymers, ethylene/vinyl acetate copolymers, silicone elastomers, medical-grade polydimethylsiloxanes, neoprene rubber, polyisobutylene, chlorinated polyethylene, polyvinyl chloride, vinyl chloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylenevinyloxyethanol copolymer; silicone copolymers, for example polysiloxane-polycarbonate copolymers, polysiloxane-polyethyleneoxide copolymers, polysiloxane-polymethacrylate copolymers, polysiloxane-polymethacrylate copolymers, polysiloxane-alkylene copolymers (e.g., polysiloxane-ethylene copolymers), polysiloxane-alkylenesilane copolymers (e.g., polysiloxaneethylenesilane copolymers), and the like; cellulose polymers, for example methyl or ethyl cellulose, hydroxypropyl methyl cellulose, and cellulose esters; polycarbonates; polytetrafluoroethylene; starches; gelatins; natural or synthetic gums; and any other natural or synthetic polymer or fiber and combinations thereof, provided that said material is selected such that it is impermeable to the opioid and the antagonist substance.

The barrier means can be in the form of a polymeric film which divides a reservoir of the opioid and the antagonist substance into a bottom compartment containing said opioid and a top compartment containing said antagonist substance. In a related embodiment, the barrier means preferably has a ripple configuration which divides said bottom compartment and said top compartment into a multiplicity of sections. This ripple configuration makes it difficult to separately remove the opioid or the antagonist substance from the dosage form for misuse and abuse of the opioid. In another embodiment said barrier means comprise a water-soluble material or a material soluble in alcohol or organic solvents which completely encapsulates discrete units of said antagonist substance, wherein said units of antagonist substance are dispersed within a substantially anhydrous medium containing said opioid.

Referring now to FIG. 1, there is shown a cross-sectional view of a dosage form of this invention comprising an adhesive layer 5 for attachment to the skin, a reservoir of opioid 3, delivery means 1 for delivering said opioid to the skin, a reservoir of opioid antagonist substance 4, and barrier means 2 separating said opioid 3 and said opioid antagonist substance 4. In this embodiment, said delivery means 1 and said adhesive layer 5 are permeable to said opioid 3. The reservoir of opioid 3 can contain from about 0.25 milligrams to about 200 milligrams of said opioid 3, as well as other optional ingredients, such as permeation enhancers, thickeners, solvents, stabilizers, excipients, carriers and the like. A reservoir of opioid antagonist substance 4 can contain a sufficient amount of said antagonist substance to substantially attenuate the euphorigenic effect of said opioid if the dosage form is ingested or substantially immersed in a solvent. The delivery means 1 can comprise a polymer film which forms a cavity containing a reservoir of said opioid 3 and said antagonist substance 4. The reservoir can contain a bottom compartment which contains said opioid 3 and a top compartment which contains said antagonist substance 4, wherein said bottom compartment is separated from said top compartment by said barrier means 2. Adhesive layer 5 is juxtaposed to the reservoir or said opioid 3 for attachment of the dosage form to the skin when the dosage form is applied to the skin, opioid 3 diffuses osmotically through delivery means 1 and adhesive layer 5. When the dosage form is ingested or immersed in a solvent, said antagonist substance 4 diffuses out of the top compartment through delivery means 1.

Figure 2:
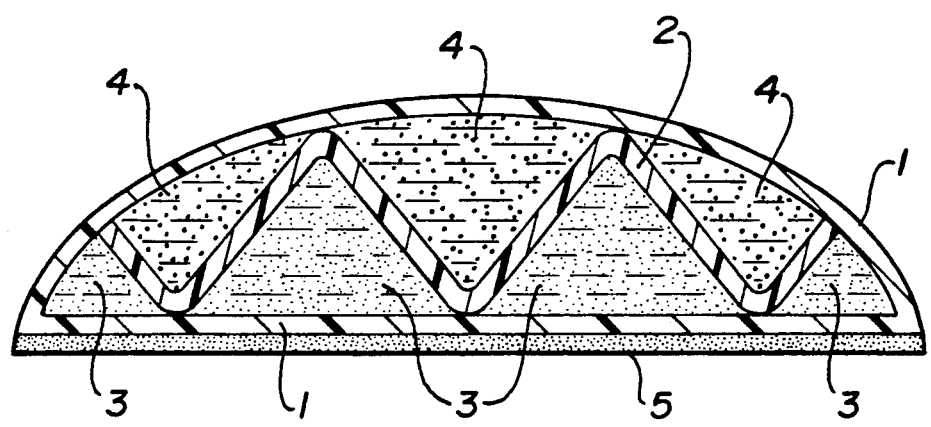
FIG. 2 shows a cross-sectional view of a dosage form of this invention comprising barrier means 2, wherein said barrier means has a ripple configuration.

Referring now to FIG. 2, there is shown a cross-sectional view of a dosage form of this invention comprising barrier means 2, wherein said barrier means 2 has a ripple configuration and divides the bottom compartment and the top compartment into a multiplicity of sections.

Figure 3:
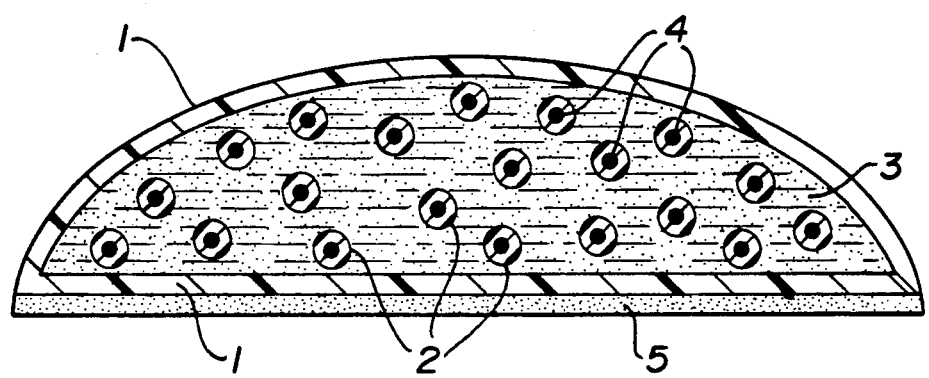
FIG. 3 shows a cross-sectional view of a dosage form of this invention wherein the opioid antagonist 4 is encapsulated by barrier means 2 and uniformly dispersed within a medium containing opioid 3.

Referring now to FIG. 3, there is shown a cross-sectional view of a dosage form of this invention wherein the opioid antagonist 4 is encapsulated by barrier means 2 and uniformly dispersed within a reservoir of opioid 3. In this embodiment, the reservoir of said opioid 3 comprises a substantially anhydrous medium and has dispersed therein one or more discrete units of said antagonist substance 4, wherein each of said units of said antagonist substance 4 is completely encapsulated by said barrier means 2. Said barrier means 2 comprise a polymer or other material which is soluble in water, alcohol or an organic solvent. Said anhydrous medium preferably comprises hydrophobic materials selected from the group consisting of lipids, mineral oil, paraffin, petrolatum, microcrystalline wax, ceresin and mixtures thereof. In this embodiment, opioid 3 diffuses osmotically through delivery means 1 and adhesive layer 5 into the skin when the dosage form is applied to the skin by said adhesive layer. If the dosage form is ingested or immersed in a solvent, such as water, alcohol or organic solvent, said barrier means 2 will be dissolved, solubilized or swelled to release said antagonist substance 4.

Figure 4:
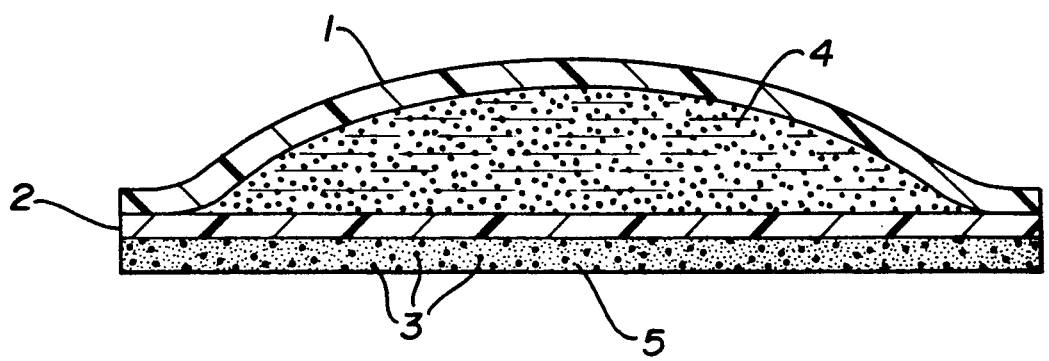
FIG. 4 shows a cross-sectional view of a dosage form of this invention, wherein opioid 3 has been uniformly dispersed within adhesive layer 5, and said adhesive layer has been attached to barrier means 2.

Referring now to FIG. 4, there is shown a cross-sectional view of a dosage form of this invention, wherein opioid 3 has been uniformly dispersed within adhesive layer 5, and said adhesive layer 5 has been attached to barrier means 2. In this embodiment said barrier means 2 comprises an impermeable polymer film having a top side and a bottom side. Said adhesive layer 5 is attached to said bottom side of said barrier means 2 and functions as the delivery means for said opioid 3. Said antagonist substance 4 is enclosed within a cavity formed by a polymeric backing layer 1 which is permeable to said antagonist substance 4 and which is attached to the top side of said barrier means 2. Polymeric backing layer 1 can be comprised of any material described earlier as suitable for said delivery means, provided that said material is permeable to said antagonist substance 4. When this dosage form is applied to the skin by said adhesive layer 5, said opioid 3 diffuses osmotically through said adhesive layer 5 to the skin. If the dosage form is ingested or immersed in a solvent, said antagonist substance 4 is released through said backing layer 1.

The dosage form of this invention is preferably used for delivering analgesic levels of opioid for the treatment of pain or therapeutic levels for the treatment of narcotic addiction in a human or animal subject by applying it to the skin of said subject. The dosage form provides sustained and continuous delivery of the opioid through the skin and into the systemic circulatory system. The dosage form is especially useful in the treatment of cocaine and heroin addiction, and preferably comprises buprenorphine or a pharmaceutically acceptable salt as the opioid and naltrexone or a pharmaceutically acceptable salt as the antagonist substance. The dosage form preferably delivers and maintains a therapeutic level in the bloodstream of the subject from about 0.1 to about 100 nanograms of buprenorphine or salt thereof per milliliter of blood plasma, preferably for a period of 24 hours or greater. Application of the dosage form is repeated as needed depending on the amount of buprenorphine or salt thereof in the dosage form.

By separating the opioid from the antagonist substance by an impermeable barrier means according to this invention, an improved misuse-resistive opioid dosage form is provided. The barrier means prevents undesirable ion exchange, chemical reactions and other adverse interactions between the opioid and the antagonist substance and the respective within which each is contained. This provides an improved and controlled delivery of the opioid from the dosage form to the skin and systemic circulatory system.

This invention includes the embodiments described herein and equivalents thereof.

I claim:

1. A dosage form for the transdermal delivery of one or more opioid to the systemic circulatory system of a mammal comprising, in combination:

a) delivery means through which said opioid is delivered to said systemic circulatory system by applying to the skin, wherein said delivery means comprises a polymeric film which is permeable to said opioid and forms a cavity containing a reservoir of said opioid;

b) one or more of said opioid being selected from the group consisting of morphine, buprenorphine and pharmaceutically acceptable salts thereof, said opioid being permeable through said delivery means and to the skin to which it is applied;

c) an effective amount of one or more antagonist substance being selected from the group consisting of naltrexone, naloxone, nalorphine, nalorphine dinicotinate, nalmefene, nadide, levallorphan, cyclazocine, amiphenazole, and pharmaceutically acceptable salts thereof, said antagonist substance sufficient to substantially attenuate the euphorigenic effect of said opioid, wherein said antagonist substance is releasable from said dosage form upon being ingested or substantially immersed in a solvent; and d) barrier means which separate said antagonist substance from said opioid, and form a plurality of microencapsulated bodies containing said antagonist substance, wherein said bodies are distributed throughout said reservoir of said opioid, said barrier means being impermeable to said opioid and to said antagonist substance.

2. The dosage form of claim 1 wherein said antagonist substance is naltrexone.

3. The dosage form of claim 1 wherein said reservoir of opioid comprises a substantially anhydrous medium having said bodies dispersed therein and further wherein said barrier means comprises a material which is soluble in water, alcohol and organic solvents.

4. The dosage form of claim 3 wherein said anhydrous medium comprises hydrophobic materials selected from the group consisting of lipids, mineral oil, paraffin, petrolatum, microcrystalline wax, ceresin and mixtures thereof.

5. The dosage form of claim 1, further comprising an adhesive layer juxtaposed to said reservoir of opioid for attachment of said dosage form to the skin.

6. The dosage form of claim 5 wherein said layer of adhesive comprises acrylic polymer selected from the group consisting of vinyl acetate/ethylene acrylate, ethyl hexyl acrylate, butyl acrylate, ethyl acrylate and mixtures thereof.

7. A dosage form for the transdermal delivery of one or more opioid to the systemic circulatory system of a mammal comprising, in combination:

a) delivery means through which said opioid is delivered to said systemic circulatory system by applying to the skin, wherein said delivery means comprises a layer of adhesive containing said opioid dispersed therein;

b) one or more of said opioid being selected from the group consisting of morphine, buprenorphine and pharmaceutically acceptable salts thereof, said opioid being permeable through said delivery means and to the skin to which it is applied;

c) an effective amount of one or more antagonist substance being selected from the group consisting of naltrexone, naloxone, nalorphine, nalorphine dinicotinate, nalmefene, nadide, levallorphan, cyclazocine, amiphenazole, and pharmaceutically acceptable salts thereof, said antagonist substance sufficient to substantially attenuate the euphorigenic effect of said opioid, wherein said antagonist substance is releasable from said dosage form upon being ingested or substantially immersed in a solvent; and d) barrier means which separate said antagonist substance from said opioid, said barrier means being impermeable to said opioid and to said antagonist substance, wherein said barrier means comprises a polymer film having a top side and a bottom side and having said layer of said adhesive attached to said bottom side thereof, and further wherein said antagonist substance is enclosed within a cavity formed by a polymeric backing film permeable to said antagonist substance and attached to the top side of said barrier means.

8. The dosage form of claim 7 wherein said antagonist substance is naltrexone.

9. The dosage form of claim 7 wherein said layer of adhesive comprises acrylic polymer selected from the group consisting of vinyl acetate/ethylene acrylate, ethyl hexyl acrylate, butyl acrylate, ethyl acrylate and mixtures thereof.

* * * * *